United States Patent [19]

Galat

[11] Patent Number: 4,783,551

[45] Date of Patent: Nov. 8, 1988

[54] POTASSIUM ACETYLSALICYLATE ADDITION COMPOUND AND PROCESS OF PREPARING

[76] Inventor: Alexander Galat, 1950 S. Ocean Dr., Hallandale, Fla. 33009

[21] Appl. No.: 868,325

[22] Filed: May 20, 1986

[51] Int. Cl.$^4$ .............................................. C07C 69/03
[52] U.S. Cl. ..................................... 560/143; 514/160
[58] Field of Search ............... 560/143; 514/163, 165; 424/43, 44

Primary Examiner—Michael L. Shippen
Attorney, Agent, or Firm—Ladas & Parry

[57] ABSTRACT

The invention is drawn to a compound of the formula

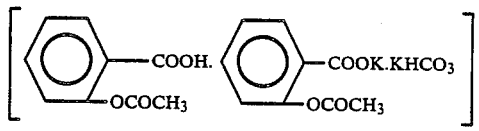

which can be prepared by the reaction of acetylsalicylic acid with potassium carbonate or potassium bicarbonate in the presence of minor amounts of water. The compound is a substantially stable solid which readily dissolves in water with the formation of a neutral solution of an aspirin salt, i.e., potassium acetylsalicylate.

12 Claims, No Drawings

POTASSIUM ACETYLSALICYLATE ADDITION COMPOUND AND PROCESS OF PREPARING

Acetylsalicylic acid (aspirin) is a valuable drug in arthritis, inflammations, analgesia, and has other useful applications. It combines high effectiveness with low toxicity and is one of the least expensive drugs available.

Unfortunately, its acid character combined with low solubility (0.3%) causes problems for many users. The insoluble particles adhere to the stomach mucosae producing irritation and inflammation as a result of which a large number of users are intolerant to aspirin (The Lancet, 8/23/80, p. 410; 9/20/80, p. 610).

In order to overcome this side-effect, a number of soluble neutral salts of acetylsalicylic acid have been prepared. Of these, sodium acetylsalicylate received most attention and is currently in commercial use (U.S. Pat. Nos. 2,211,485; 3,064,038; 3,109,019; 3,985,792; German Pat. No. 218,467; Ger. No. 270,326). This sodium salt is, however, difficult and expensive to prepare and, in addition, being very hygroscopic, is difficult to handle and keep stable. Minor amounts of contamination with moisture such as might normally occur in processing, packaging, or in the course of its use by consumers, produce a rapid and extensive decomposition with formation of acetic and salicylic acids, both of which are irritating to the stomach.

Another approach to transform aspirin into a neutral soluble form was to prepare mixtures of this acid with solid neutralizing compounds such as alkaline bicarbonates, carbonates and hydroxides. For reasons of high alkalinity, the latter two groups of compounds were unsuitable, and for practical purposes only alkaline metal bicarbonates could be considered. Of these mixtures, acetylsalicylic acid with sodium bicarbonate received most attention.

However, aspirin is incompatible with metal bicarbonates. This incompatibility is of both a physical and chemical nature. The physical deterioration manifests itself by the mixtures, which initially are in a dry loose powder condition, becoming on standing a sticky solid mass evolving carbon dioxide and producing an acetic acid odor. Obviously, such products thus become unsuitable for practical medicinal use.

The chemical deterioration results from internal chemical reactions between the two components of such mixtures and is evidenced by formation of salicylic and acetic acids, both diminishing the therapeutic effect of the product, and producing stomach irritation which the product was designed to eliminate.

Nevertheless, it was possible by use of certain special techniques to render such mixtures, especially aspirin and sodium bicarbonate, relatively stable and such products are in commercial use.

In order to prevent deterioration, particles of such mixtures are coated in order to prevent their intimate contact with each other. This operation is expensive and adds substantially to the cost of the product.

In general, without such special measures mixtures of aspirin with alkaline bicarbonates deteriorate very rapidly, sometimes in a matter of days, with production of pressure in the container caused by formation of carbon dioxide.

However, with or without such special techniques, it has been found necessary to use an excess of bicarbonate in order to assure rapid and complete dissolution. In commercial products now on the market—mostly all of them based on formation of sodium acetylsalicylate—the presence of a large sodium content is detrimental to a number of users, particularly geriatrics.

To summarize, all previous methods to produce acetylsalicylic acid in a neutral watersoluble form suffer from various disadvantages. As pointed out above, sodium acetylsalicylate has received the most attention and is commercially available. Its disadvantage (as is the case with all metal salts of acetylsalicylic acid) is its hygroscopicity which eventually leads to decomposition. In the case of physical mixtures of acetylsalicylic acid with bicarbonates, the most studied composition is with sodium bicarbonate. As mentioned, excessively large amounts of the bicarbonate are required, increasing the undesirable sodium content to a high level.

In all cases, whether dealing with pre-formed salts of acetylsalicylic acid or with its mixtures with bicarbonates, operations are complicated, expensive, and lead to products of relatively high cost.

The object of the present invention is to provide a solid composition of matter, substantially stable, of low cost, and readily soluble in water with formation of a neutral solution of an aspirin salt.

It is well-known that acetylsalicylic acid reacts with an equivalent amount of potassium carbonate in water to form neutral potassium acetylsalicylate (for example, Ann. 406, p. 241):

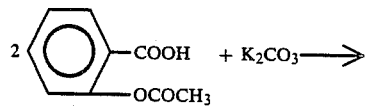

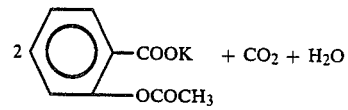

I have discovered, however, that when this interaction is conducted in presence of minor amounts of water, the following new and unexpected reaction takes place:

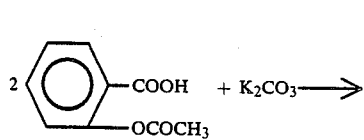

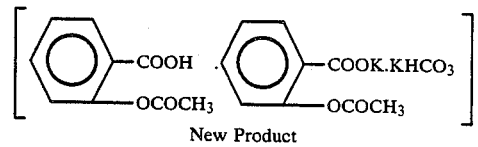

New Product

The unique and unexpected aspect of this novel chemical reaction is that in contrast to classical chemistry, where an acid reacting with a carbonate forms a salt and carbon dioxide, in the present case there is no formation of carbon dioxide and the product of the reaction is what is believed to be a chemical complex of unusual molecular structure.

The product of this reaction, a composition which may be a new chemical compound, adduct or complex accomplishes the objects of the present invention. It is a solid product, substantially stable, and of low cost; it readily dissolves in water with formation of a neutral solution of an aspirin salt, i.e. potassium acetylsalicylate.

Preparation of this composition is illustrated by the following examples:

EXAMPLE 1

100 gm (0.55 Moles) of acetylsalicylic acid (mesh #40) 38 gm of potassium carbonate (0.27 Moles), and 32 ml of water were stirred for one hour at room temperature. To the resulting mixture was added 200 ml of acetone and the stirring continued for another 15 minutes. The solid product was filtered, washed with a mixture of 8 ml of water and 32 ml of acetone, followed by anhydrous acetone. The product was dried in the air, and finally in a vacuum dessicator over calcium chloride.

The yield was 94.5 gm (68.5% of the theory).

EXAMPLE 2

100 gm (0.55 Moles) of acetylsalicylic acid, (mesh #40) was stirred with 350 ml of acetone and to the resulting solution was added slowly with stirring a solution of 38 gm (0.27 Moles) of potassium carbonate in 32 ml of water.

The crystalline precipitate that was formed, was filtered, washed with acetone and air dried.

The yield was 108 gm (77.7% of the theory).

EXAMPLE 3

100 gm (0.55 Moles) of acetylsalicylic acid, (mesh #40) 38 gm (0.27 Moles) of potassium carbonate, and 32 ml of water were stirred for 1 hour. To the resulting mixture was added 300 ml of isopropanol, and the mixture stirred an additional 15 minutes. The solid product was filtered, washed with isopropanol, followed by an acetone wash and air-dried.

The yield was 106 gm (77% of the theory). This reaction was run with aspirin mesh #40 but other meshes or micronized aspirin may be used. The reaction may be faster with finer meshes.

EXAMPLE 4

50 gm (0.275 Moles) of acetylsalicylic acid (mesh #80) were stirred with 175 ml of acetone. The temperature of this mixture dropped to 15° C. and the acid went partially in solution. A solution of 19 gm (0.135 Moles) of potassium carbonate in 17 ml of water was added slowly, with stirring to the acid-acetone mixture. A crystalline precipitate formed while the temperature rose to 27° C. The mixture was cooled to 7°-8° C., filtered, the solid washed with three portions of acetone, 25 ml each, and air-dried. The yield of the product was 61 gm (88% of the theory).

EXAMPLE 5

20 gm Of acetylsalicylic acid, 8 gm of potassium carbonate and 10 ml of water were stirred at room temperature for one hour. Twenty ml of acetone was then added, the mixture stirred for 10 minutes, filtered, washed with acetone and air-dried.

Yield: 16.6 gm (59% of theory).

In examples given, the amount of acetone varies between 100 and 350 parts by volume per 100 gm of acetylsalicylic acid illustrating the lower range of the solvent, whether used as a precipitant or in reaction medium. The operative range is 100-1000 parts by volume per 100 parts of acetylsalicylic acid. The preferred amounts are, of course, a matter of manufacturing economics.

In Example 2 and 4, a solution of potassium carbonate is used. In order to obtain good yield without using excessive amount of solvent, the amount of water should be kept to a minimum. Accordingly a saturated solution of potassium carbonate is used. Since the solubility depends on the ambient temperature, occassionally a small amount of crystals may form and, in this case, a slight warming of the mixture may be needed to bring these crystals into solution. It must be mentioned that the dissolution of anhydrous potassium carbonate in water is very exothermic which helps the dissolution. When the solution is complete, the mixture must be cooled to about room temperature and in this cooling step formation of crystals should be avoided. If it does occur, a slight rewarming may become necessary, as mentioned above.

It must be mentioned further, that in Examples 2 and 4, for economical reasons, the amount of acetone used is small and not sufficient to completely dissolve the acetylsalicylic acid. However, as the reaction progresses the entire amount goes into solution.

EXAMPLE 6

20 gm (0.11 Moles) of acetylsalicylic acid (mesh #80), 11.1 gm (0.11 Moles) of potassium bicarbonate, 20 ml of acetone and 5 ml of water were stirred together. The temperature of the mixture was brought gradually to 50° C. and maintained there until the evolution of carbon dioxide became negligible (about 15 minutes). There was added an additional 60 ml of acetone, the mixture filtered and the solid washed with several portions of acetone, 25 ml each, and air-dried. The yield of the product was 9.6 gm (34.8% of the theory).

Process Parameters

Acetone and isopropanol are the preferred precipitants for the product of this invention. Other solvents may be used but are not as preferred for certain reasons. Lower alcohols are less suitable because of the product's considerable solubility in these solvents, particularly in presence of the water that was used for the reaction. Alcohols such as butanols, particularly t-butanol, may be used but have disadvantages of cost, difficulty of recovery and odor. The same objections hold for ketones higher than acetone. Solvents such as bifunctional alcohols and ethers ("Cellosolves") are, again, less suitable because of cost and difficulty in recovery.

Description of product and characteristics of its behavior

The product is a fine crystalline white powder, non-hygroscopic to about 80–85% relative humidity, readily soluble in water with evolution of carbon dioxide. It is very soluble is methanol (about 35 gm in 100 ml), in acetone containing 10–15% of water (about 13 gm in 100 ml), insoluble in ketones and most organic solvents.

Melting point: The substance becomes wet at about 115° C.; there is rapid evolution of gas at about 120° C., followed by re-solidification; at about 190°–195° C. the product melts with formation of bubbles.

The stability of the compound of this invention was established by the standard accelerated aging procedure in which samples of the product are kept at 37°-38° C. At this temperature, 3 months correspond to about 2 years at room temperature. In such tests with aspirin preparations, the percent free salicylate formed is usually taken as an index of the percent decomposition.

With the compound of this invention, 3 months at 37°-38° C. showed a free salicylate content of 2%, on the average, which was confirmed by an assay of 98%.

In addition all samples remained odorless, clearly soluble in water, and in no case was pressure developed in the container (indicating an absence of carbon dioxide formation).

The chemical composition of the new compound was established as follows:

The product was dissolved in water, and acetylsalicylic acid precipitated by hydrochloric acid. The acetylsalicylic acid content was found to be 71% (theory: 72%).

The presence of acetylsalicyclic acid and potassium acetylsalicylate in the molecule of the new compound was established by dissolving the compound in acetone containing about 15% by volume of water, and allowing the acetone to evaporate. Crystals which separated were filtered and dried and had a melting point of 168°-170° C., were sparingly soluble in water, and contained, upon acidification, 88-89% of acetylsalicylic acid (theory: 90%). All these data are characteristic of the acid potassium acetylsalicylate (one mole acetylsalicylic acid—one mole potassium acetylsalicylate).

Presence of potassium bicarbonate in the filtrate from the preceding experiment was established by the usual analytical methods (potassium content, measurement of carbon dioxide produced by acidification as well as its water solubility and alkaline reaction).

Finally, the composition was confirmed by dissolving the compound of this invention in water, and isolating and characterizing potassium acetylsalicylate dihydrate by methods described in the literature.

Thus, 2 gram of the product were dissolved in 1 ml of water and to the slightly turbid solution was added 10 ml of acetone. The resulting clear solution was kept at −10° C. overnight, the crystalline precipitate filtered, washed with acetone and air dried. The product had the melting point, solubility and all other characteristics of the potassium acetylsalicylate dihydrate.

The potassium content of the product of the present invention was 15.8% (Theory 15.9%).

The instant composition (compound, adduct or complex) may also be prepared, for example, by additional methods; (see Example 5) such as:

a reaction between aspirin and potassium bicarbonate:

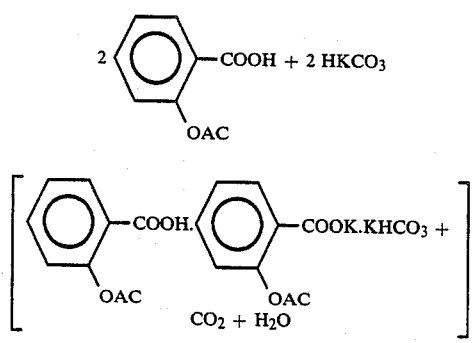

The new composition of this invention appears to be a chemical complex of which the fine structure and the bonding of its component molecules remains to be elucidated. It is stable in organic solvents, such as methanol, and in mixtures of solvents containing small amounts of water. This is evidenced by the fact that there is no formation of carbon dioxide and no precipitation of the components of the molecule which, individually, may be insoluble or sparingly soluble in such solvents (for example, methanol and acetone-water mixtures). Of course, when mentioning stability in this context, it must be kept in mind that in solvents such as methanol or solvents containing water, a trans-esterification and hydrolytic decomposition will in time inevitably take place.

In the presence of water, however, the compound readily dissociates into its components and a reaction producing potassium acetylsalicylate and carbon dioxide takes place:

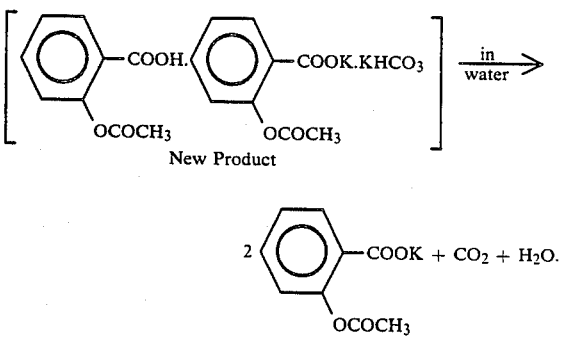

COMPARISON OF PRODUCT WITH PHYSICAL MIXTURE OF PRODUCT COMPONENTS

An intimate mixture of equimolar amounts of acetylsalicylic acid, anhydrous potassium acetylsalicylate and potassium bicarbonate was prepared and used in these comparison experiments.

a. The effect of water

Since the composition of this invention contains two water-soluble moieties (potassium acetylsalicylate and potassium bicarbonate) and one nearly insoluble (acetylsalicylic acid) it could have been expected that on addition of water a mere physical mixture would separate into its soluble and insoluble parts. This indeed proved to be the case as the following experiment shows:

One gram of the physical mixture was stirred with 10 ml of water and the insoluble portion was filtered, washed with water and dried. It had the melting point of 135°-136° C., which was not depressed by the admixture of an authentic sample of acetylsalicylic acid. The melting point of the latter given in the literature is 135° C.

Under identical conditions the product of the present invention rapidly dissolves in water giving a clear solution free of insoluble matter.

b. The effect of ambient moisture

Since one of the moieties of the product of the present invention is highly hygroscopic (potassium acetylsalicylate absorbs moisture from the air with the formation of di-hydrate), a physical mixture containing this ingredient should exhibit the same property. This proved to be the case. The physical mixture of equimolar amounts of the three compounds exposed to the air of 45% Relative humidity gained 5-6% in weight. Calculated: 6.1%.

By contrast, the product of this invention under the same conditions showed no gain in weight. This indicates that in the product of this invention the strongly hygroscopic potassium acetylsalicylate is chemically (or otherwise) bound and has lost the property of forming a hydrate in the presence of moisture.

c. The effect of treatment with acetone

Since one of the moieties of the product of this invention (acetylsalicylic acid) is very soluble in acetone, and another one (potassium acetylsalicylate) is somewhat soluble also, while the third (potassium bicarbonate) is almost completely insoluble, it was expected that acetone would extract a substantial amount of soluble materials from the physical mixture. This, in fact, was the case, as the following experiment shows.

One gram of the physical mixture was shaken with 10 ml of acetone and the insoluble portion filtered, washed with acetone and dried. It weighed 0.45 g, indicating that 0.55 g went into solution. The latter was evaporated to dryness and the crystalline residue was found to weigh 0.47 g., melting point 125°–130° C. (acetylsalicylic acid: 135° C.). The crystals were washed with water to remove any potassium acetylsalicylate, which raised the melting point to 135° C. However the melt did not become clear until 170° C. indicating the presence of some acid potassium acetylsalicylate (melting point 170° C.). Obviously, the extracted potassium acetylsalicylate interacted with the extracted acetylsalicylic acid to form partly the acid salt.

The acetone-insoluble portion (0.45 gm) was soluble in water without evolution of carbon dioxide, indicating that all acetylsalicylic acid was extracted, as was expected, and the solid consisted of potassium acetylsalicylate and potassium bicarbonate.

On the other hand, when 1 g of the product of the present invention was similarly treated with 10 ml of acetone the insoluble residue was 1 g, showing that it contained no acetone-soluble portion, in contrast to the physical mixture of the components. It was readily soluble in water with evolution of carbon dioxide and had all other characteristics of the product of this invention.

This experiment, again, indicates that the product of this invention is not a physical mixture.

d. Solubility experiments with organic solvents

The product of this invention is soluble in methanol to the extent of about 35 g in 100 ml. Now, 35 gm of the product has a potassium bicarbonate content of 7 gm Yet, the solubility of potassium bicarbonate itself in 100 ml of methanol is practically nil (0.1 gm in 100 ml of methanol remains almost all undissolved). Thus, the 7 gm of potassium bicarbonate which is held in solution in 100 ml of methanol must be chemically (or otherwise) bound.

Similarly, it was found that 100 mls of a mixture of 200 ml of acetone and 32 ml of water will dissolve 30 gm of the product of this invention. This amount contains 6 gm of potassium bicarbonate, yet the solubility of potassium bicarbonate in this mixture is less than 1 gm, when tested alone.

Thus, experimental evidence precludes the possibility that the product of this invention is a physical mixture composed of acetylsalicylic acid, potassium acetylsalicylate and potassium bicarbonate and strongly suggests that its three compounds are chemically (or otherwise) bound in equimolecular proportions.

Nevertheless, consideration was given to the possibility that it was a physical mixture of two compounds: acid potassium acetylsalicylate (acetylsalicylic acid . potassium acetylsalicylate) and potassium bicarbonate. However, the evidence provided by the solubility experiments with organic solvents cited above precludes also this possibility. This is supported by the following additional evidence:

35 gm of the product, corresponding to 28 gm of the acid salt, is soluble in 100 ml of methanol. Yet, when tested alone, only 6.5 gm of the acid salt is soluble in this amount of methanol.

Similarly, a mixture of 200 ml of acetone and 32 ml of water dissolves 30 gm of the product, which corresponds to 24 gm of the acid salt. Yet, when tested alone, this salt is practically insoluble in this solvent mixture.

e. Melting point profiles

Melting point behavior of physical mixtures of equimolar amounts of components and that of the product of this invention are given below. (Mixture #1: acetylsalicylic acid-potassium acetylsalicylate-potassium bicarbonate. Mixture #2: acid potassium acetylsalicylate-potassium bicarbonate).

| Temperature° (C.) | Mixture #1 | Mixture #2 | Product |
|---|---|---|---|
| 115° | | wet | wet |
| 120° | wet | wet | rapid, massive evolution of gas followed by re-solidification |
| 135–140° | partial, turbid melt | | |
| 145° | | sl. melting | |
| 150°–155° | clear melt | clear melt | |
| 170° | no change, very slow formation of bubbles | no change, very slow formation of bubbles | |
| 190° | | | melts, rises, bubbles |
| 195–6° | | | clear melt |

The most significant difference in the melting behavior is the rapid, massive evolution of gas which occurs at 120° C. with the product of this invention, as well as the resolidification and melting at 195°–196° C., both of which are absent in the physical mixtures of the components.

The experimental evidence presented above strongly supports the view that the product of this invention is a chemical compound, rather than a physical mixture. However, whether the product of this invention is a compound, a complex or an adduct, or even a physical coprecipitate of the components, is of course, immaterial insofar as its useful storage properties, solubilities, and medicinal value is concerned.

Whereas the use of acetylsalicylic acid (aspirin) in arthritis, inflammations and analgesia is well known, it is of interest to mention that recent large-scale clinical studies show it to be an effective agent in preventing strokes. It is also of interest to mention that similar studies indicate that potassium, also, is effective in preventing strokes, although the mechanism of its action is different from that of acetylsalicylic acid. They thus complement each other and the combination of these two pharmacological effects in a single chemical molecule, such as in the product of this invention, is of considerable potential value. Further clinical studies may reveal synergism. Needless to add, strokes are one of the major causes of mortality in humans.

This invention provides, for the first time, a stable, relatively non-hygroscopic and a low cost product which offers potassium acetylsalicylate for practical commercial use in the management of arthritis, inflammations, analgesia and other afflictions for which acetylsalicylic acid (aspirin) is normally used.

I claim:

1. A compound of the formula

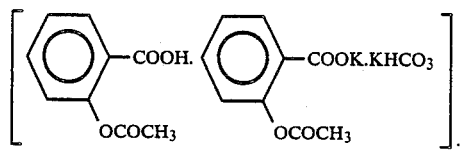

2. A process for preparing a compound of the formula

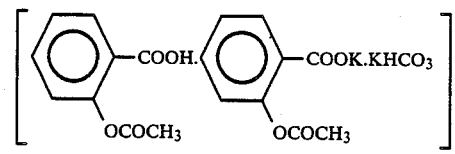

which comprises
   (a) reacting about 1 mole of acetylsalicylic acid with about one-half mole of potassium carbonate in about 45 to 75 ml. of water at a temperature in the range of about 15° C. to 40° C. and
   (b) recovering the product from the reaction mixture.

3. A process according to claim 2, wherein the reaction in step (a) is carried out in the presence of an organic solvent.

4. A process according to claim 3, wherein said organic solvent comprises acetone.

5. A process as in claim 2, wherein said product is recovered by precipitation with an organic solvent.

6. A process according to claim 2, wherein said mixture is cooled after step (a).

7. A process according to claim 5, in which said organic solvent is selected from the group consisting of a lower alkanol of 1 to 4 carbon atoms and acetone and mixtures of these.

8. A process according to claim 5, in which said organic solvent is acetone.

9. A process according to claim 5, in which said organic solvent is isopropanol.

10. A process for preparing a compound of the formula

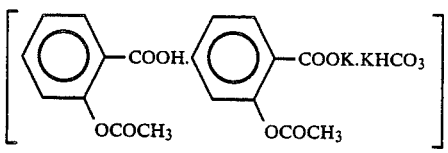

which comprises
   (a) stirring together about 1 mole of acetylsalicylic acid with about 1 mole of potassium bicarbonate, about 200 mls of acetone and about 50 mls of water at a temperature in the range of 20°–50°, and
   (b) recovering the product from the reaction mixture.

11. A compound of the formula

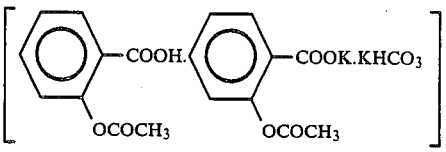

said compound being prepared by a process comprising
   (a) reacting about 1 mole of acetylsalicylic acid with about one-half mole of potassium carbonate in about 45 to 75 ml. of water at a temperature in the range of about 15° C. to 40° C. and
   (b) recovering the product from the reaction mixture.

12. A compound of the formula

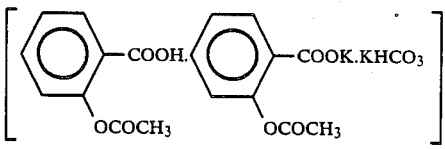

said compound being prepared by a process comprising
   (a) stirring together about 1 mole of acetylsalicylic acid with about 1 mole of potassium bicarbonate, about 200 mls of acetone and about 50 mls of water at a temperature in the range of 20°–50°, and
   (b) recovering the product from the reaction mixture.

* * * * *